US011266343B2

(12) United States Patent
Iglesias

(10) Patent No.: US 11,266,343 B2
(45) Date of Patent: Mar. 8, 2022

(54) TREATMENT OF FECAL INCONTINENCE

(71) Applicant: Remendium Labs LLC, Baton Rouge, LA (US)

(72) Inventor: Ramon Jose Iglesias, DeLeon Springs, FL (US)

(73) Assignee: Remendium Labs LLC, Baton Rouge, LA (US)

( * ) Notice: Subject to any disclaimer, the term of this patent is extended or adjusted under 35 U.S.C. 154(b) by 118 days.

(21) Appl. No.: 15/626,949

(22) Filed: Jun. 19, 2017

(65) Prior Publication Data

US 2017/0303843 A1 Oct. 26, 2017

Related U.S. Application Data

(63) Continuation of application No. 14/581,547, filed on Dec. 23, 2014, now abandoned, which is a continuation-in-part of application No. 14/359,890, filed as application No. PCT/US2012/066613 on Nov. 27, 2012, now abandoned.

(60) Provisional application No. 61/563,889, filed on Nov. 28, 2011.

(51) Int. Cl.
*A61B 5/00* (2006.01)
*A61B 5/22* (2006.01)

(52) U.S. Cl.
CPC .......... *A61B 5/4255* (2013.01); *A61B 5/0036* (2018.08); *A61B 5/227* (2013.01); *A61B 5/6852* (2013.01); *A61B 5/6898* (2013.01)

(58) Field of Classification Search
CPC ................... A61B 5/202; A61B 5/205; A61B 2018/00517; A61B 2018/00523; A61B 5/036
See application file for complete search history.

(56) References Cited

U.S. PATENT DOCUMENTS

| 2,830,582 | A | 4/1958 | Ljung |
| 3,854,476 | A | 12/1974 | Dickinson III et al. |
| 4,669,478 | A | 6/1987 | Robertson |

(Continued)

FOREIGN PATENT DOCUMENTS

| CA | 2625428 A1 | 7/2007 |
| CA | 2862928 A1 | 8/2013 |

(Continued)

OTHER PUBLICATIONS

Korvink, et al. (2006). MEMS—A Practical Guide to Design, Analysis, and Applications. William Andrew Publishing/Noyes. Ch. 17, p. 901-942. Retrieved from https://app.knovel.com/hotlink/toc/id:kpMEMSAPG2/mems-practical-guide/mems-practical-guide (Year: 2006).*

(Continued)

*Primary Examiner* — David J. McCrosky
(74) *Attorney, Agent, or Firm* — Clark & Elbing LLP

(57) ABSTRACT

Methods and devices to diagnose and treat fecal incontinence in females and males are provided. A multiple sensor-enabled catheter for positioning in a patient's rectum allows for the visualization and manipulation or positioning of an anatomical reference point(s) in the patient's body. A multiple sensor-enabled catheter for rectal insertion in a patient allows for the visualization and implementation of efficient and effective exercises to strengthen pelvic floor muscles.

11 Claims, 1 Drawing Sheet

(56) References Cited

U.S. PATENT DOCUMENTS

| | | | |
|---|---|---|---|
| D309,866 S | 8/1990 | Fukuda et al. | |
| D310,275 S | 8/1990 | Su | |
| 5,328,077 A | 7/1994 | Lou | |
| 5,386,836 A | 2/1995 | Biswas | |
| 5,406,961 A | 4/1995 | Artal | |
| 5,562,717 A | 10/1996 | Tippey | |
| 5,603,685 A | 2/1997 | Tutrone, Jr. | |
| 5,674,238 A | 10/1997 | Sample et al. | |
| 5,924,984 A | 7/1999 | Rao | |
| 6,001,060 A | 12/1999 | Churchill et al. | |
| 6,021,781 A | 2/2000 | Thomson et al. | |
| 6,039,701 A | 3/2000 | Sliwa et al. | |
| 6,056,699 A * | 5/2000 | Sohn | A61B 5/202 600/561 |
| 6,086,549 A | 7/2000 | Neese et al. | |
| 6,264,582 B1 | 7/2001 | Remes | |
| 6,272,371 B1 | 8/2001 | Shlomo | |
| D458,681 S | 6/2002 | Sherlock et al. | |
| 6,413,206 B2 | 7/2002 | Biswas | |
| 6,432,037 B1 | 8/2002 | Eini et al. | |
| 6,511,427 B1 | 1/2003 | Sliwa, Jr. et al. | |
| 6,672,996 B2 | 1/2004 | Ross et al. | |
| 6,679,854 B2 | 1/2004 | Honda et al. | |
| D491,079 S | 6/2004 | Lim | |
| 6,816,744 B2 | 11/2004 | Garfield et al. | |
| 7,079,882 B1 | 7/2006 | Schmidt | |
| D535,203 S | 1/2007 | Chen | |
| 7,577,476 B2 | 8/2009 | Hochman et al. | |
| 7,608,037 B2 | 10/2009 | Levy | |
| 7,628,744 B2 | 12/2009 | Hoffman et al. | |
| 7,645,220 B2 | 1/2010 | Hoffman | |
| 7,736,298 B2 | 6/2010 | Guerquin et al. | |
| 7,837,682 B2 | 11/2010 | Ostrovsky et al. | |
| 7,955,241 B2 | 6/2011 | Hoffman et al. | |
| 7,957,794 B2 | 6/2011 | Hochman et al. | |
| D651,531 S | 1/2012 | Rothman | |
| 8,147,429 B2 | 4/2012 | Mittal et al. | |
| 8,360,954 B2 | 1/2013 | Kim | |
| 8,623,004 B2 | 1/2014 | Johnson et al. | |
| 8,715,204 B2 | 5/2014 | Webster et al. | |
| 8,728,140 B2 | 5/2014 | Feemster et al. | |
| 8,740,767 B2 | 6/2014 | Rosen et al. | |
| 8,805,472 B2 | 8/2014 | Iglesias | |
| 8,821,407 B2 | 9/2014 | Kirsner | |
| 8,914,111 B2 | 12/2014 | Haessler | |
| 8,983,627 B2 | 3/2015 | Pelger et al. | |
| 9,155,885 B2 | 10/2015 | Wei et al. | |
| 9,248,285 B2 | 2/2016 | Haessler | |
| 9,381,351 B2 | 7/2016 | Haessler | |
| 9,408,685 B2 | 8/2016 | Hou et al. | |
| 9,656,067 B2 | 5/2017 | Pelger et al. | |
| 9,861,316 B2 | 1/2018 | Egorov | |
| 9,974,635 B2 | 5/2018 | Rosen et al. | |
| D832,437 S | 10/2018 | Zeltwanger et al. | |
| D845,478 S | 4/2019 | Luke | |
| D852,069 S | 6/2019 | Fu | |
| D853,035 S | 7/2019 | Moretti | |
| 10,470,862 B2 | 11/2019 | Iglesias | |
| D888,949 S | 6/2020 | Beer et al. | |
| D889,649 S | 7/2020 | Beer et al. | |
| D893,026 S | 8/2020 | Leather | |
| D896,958 S | 9/2020 | Beer et al. | |
| D896,959 S | 9/2020 | Beer et al. | |
| D897,530 S | 9/2020 | Beer et al. | |
| D898,911 S | 10/2020 | Beer et al. | |
| D899,593 S | 10/2020 | Beer et al. | |
| D908,160 S | 1/2021 | Sun | |
| D909,679 S | 2/2021 | Chen | |
| D910,851 S | 2/2021 | Lagrange et al. | |
| 2001/0001125 A1 | 5/2001 | Schulman et al. | |
| 2001/0047132 A1 | 11/2001 | Johnson et al. | |
| 2002/0022836 A1 | 2/2002 | Goble et al. | |
| 2002/0111586 A1 | 8/2002 | Mosel et al. | |
| 2003/0028180 A1 | 2/2003 | Franco | |
| 2004/0236223 A1 | 11/2004 | Barnes et al. | |
| 2004/0260207 A1 | 12/2004 | Eini et al. | |
| 2005/0148447 A1 | 7/2005 | Nady | |
| 2005/0177067 A1 | 8/2005 | Tracey et al. | |
| 2006/0036188 A1 | 2/2006 | Hoffman et al. | |
| 2006/0074289 A1 | 4/2006 | Adler et al. | |
| 2006/0084848 A1 | 4/2006 | Mitchnick | |
| 2006/0211911 A1 | 9/2006 | Jao et al. | |
| 2007/0066880 A1 | 3/2007 | Lee et al. | |
| 2007/0232882 A1 | 10/2007 | Glossop et al. | |
| 2007/0255090 A1 | 11/2007 | Addington et al. | |
| 2007/0265675 A1 | 11/2007 | Lund et al. | |
| 2007/0270686 A1 | 11/2007 | Ritter et al. | |
| 2008/0077053 A1 | 3/2008 | Epstein et al. | |
| 2008/0139876 A1 | 6/2008 | Kim | |
| 2008/0146941 A1 | 6/2008 | Dala-Krishna | |
| 2008/0149109 A1 | 6/2008 | Ziv | |
| 2008/0154131 A1 | 6/2008 | Lee et al. | |
| 2008/0171950 A1 | 7/2008 | Franco | |
| 2008/0300658 A1 | 12/2008 | Meskens | |
| 2009/0149740 A1 | 6/2009 | Hoheisel | |
| 2009/0216071 A1 | 8/2009 | Zipper | |
| 2009/0270963 A1 | 10/2009 | Pelger et al. | |
| 2009/0306509 A1 | 12/2009 | Pedersen et al. | |
| 2010/0069784 A1 | 3/2010 | Blaivas | |
| 2010/0174218 A1 | 7/2010 | Shim | |
| 2010/0222708 A1 | 9/2010 | Hitchcock et al. | |
| 2010/0249576 A1 | 9/2010 | Askarinya et al. | |
| 2010/0262049 A1 | 10/2010 | Novak et al. | |
| 2011/0054357 A1 | 3/2011 | Egorov et al. | |
| 2011/0077500 A1 | 3/2011 | Shakiba | |
| 2011/0190580 A1 | 8/2011 | Bennett et al. | |
| 2011/0190595 A1 | 8/2011 | Bennett et al. | |
| 2011/0196263 A1 | 8/2011 | Egorov et al. | |
| 2012/0016258 A1 | 1/2012 | Webster et al. | |
| 2012/0265044 A1 | 10/2012 | Broens | |
| 2012/0265049 A1 | 10/2012 | Iglesias | |
| 2013/0035611 A1 | 2/2013 | White | |
| 2013/0053627 A1 | 2/2013 | Bercovich et al. | |
| 2013/0144191 A1 | 6/2013 | Egorov et al. | |
| 2013/0184567 A1 | 7/2013 | Xie et al. | |
| 2013/0192606 A1 | 8/2013 | Ziv et al. | |
| 2013/0237771 A1 | 9/2013 | Runkewitz et al. | |
| 2013/0324380 A1 | 12/2013 | Horsley | |
| 2014/0066813 A1 | 3/2014 | Daly et al. | |
| 2014/0073879 A1 | 3/2014 | Cantor et al. | |
| 2014/0088471 A1 | 3/2014 | Leivseth et al. | |
| 2014/0155225 A1 | 6/2014 | Sedic | |
| 2014/0213927 A1 | 7/2014 | Webster et al. | |
| 2014/0296705 A1 | 10/2014 | Iglesias | |
| 2014/0309550 A1 | 10/2014 | Iglesias | |
| 2015/0032030 A1 | 1/2015 | Iglesias | |
| 2015/0112230 A1 | 4/2015 | Iglesias | |
| 2015/0133832 A1 | 5/2015 | Courtion et al. | |
| 2015/0196802 A1 | 7/2015 | Siegel | |
| 2015/0282763 A1 | 10/2015 | Rosenshein | |
| 2016/0008664 A1 | 1/2016 | Siegel | |
| 2016/0022198 A1 | 1/2016 | De Laat | |
| 2016/0051354 A1 | 2/2016 | Patankar et al. | |
| 2016/0074276 A1 | 3/2016 | Scheuring et al. | |
| 2016/0121105 A1 | 5/2016 | Lee et al. | |
| 2016/0346610 A1 | 12/2016 | Iglesias et al. | |
| 2017/0281072 A1 | 10/2017 | Iglesias | |
| 2017/0281299 A1 | 10/2017 | Iglesias | |
| 2017/0291012 A1 | 10/2017 | Iglesias | |
| 2017/0312530 A1 | 11/2017 | Schilling et al. | |
| 2017/0332959 A1 | 11/2017 | Bartlett | |
| 2018/0021121 A1 | 1/2018 | Zeltwanger et al. | |
| 2019/0133738 A1 | 5/2019 | Rosen et al. | |
| 2019/0160332 A1 | 5/2019 | Beer et al. | |
| 2020/0029812 A1 | 1/2020 | Govari et al. | |
| 2020/0069161 A1 | 3/2020 | Schentag et al. | |
| 2020/0405142 A1 | 12/2020 | Whitaker | |

FOREIGN PATENT DOCUMENTS

| | | |
|---|---|---|
| CN | 204839545 U | 12/2015 |
| DE | 10345282 B3 | 4/2005 |
| DE | 202018103016 U1 | 6/2018 |
| EP | 0268972 A2 | 6/1988 |

(56) References Cited

FOREIGN PATENT DOCUMENTS

| | | |
|---|---|---|
| EP | 02689724 A1 | 1/2014 |
| GB | 2492754 A | 1/2013 |
| JP | 2002-143133 A | 5/2002 |
| JP | 2009-538176 A | 11/2009 |
| JP | 2011-183167 A | 9/2011 |
| RU | 2307636 C1 | 10/2007 |
| WO | WO-96/05768 A1 | 2/1996 |
| WO | WO-99/05963 A1 | 2/1999 |
| WO | WO-00/09013 A1 | 2/2000 |
| WO | WO-00/23030 A1 | 4/2000 |
| WO | WO-01/37732 A1 | 5/2001 |
| WO | WO-02/17987 A2 | 3/2002 |
| WO | WO-2006/107930 A2 | 10/2006 |
| WO | WO-2007/136266 A1 | 11/2007 |
| WO | WO-2010/131252 A2 | 11/2010 |
| WO | 2011/050252 A1 | 4/2011 |
| WO | WO-2011/121591 A2 | 10/2011 |
| WO | WO-2011/159906 A2 | 12/2011 |
| WO | WO-2012/079127 A1 | 6/2012 |
| WO | WO-2012/138232 A1 | 10/2012 |
| WO | WO-2013/082006 A1 | 6/2013 |
| WO | WO-2013/116310 A1 | 8/2013 |
| WO | WO-2015/103629 A1 | 7/2015 |
| WO | WO-2016/026914 A2 | 2/2016 |
| WO | WO-2016/042310 A1 | 3/2016 |
| WO | WO-2016/067023 A1 | 5/2016 |
| WO | WO-2016/119002 A1 | 8/2016 |
| WO | WO-2017/149688 A1 | 9/2017 |
| WO | WO-2018/023037 A1 | 2/2018 |
| WO | WO-2019/084468 A1 | 5/2019 |
| WO | WO-2019/084469 A1 | 5/2019 |
| WO | WO-2020/092343 A1 | 5/2020 |

OTHER PUBLICATIONS

Glazer et al., "Pelvic floor biofeedback in the treatment of urinary incontinence: A literature review." Applied Psychophysiology and Biofeedback 31.3 (2006): 187-201.
Gray's Anatomy, 39th ed., p. 1290, definition of "Bladder neck."
International Search Report and Written Opinion, dated Feb. 6, 2013, in related International Application No. PCT/US2012/066613, filed, Nov. 27, 2012.
Parekh et al., "The role of pelvic floor exercises on post-prostatectomy incontinence." The Journal of Urology 170.1 (2003): 130-133.
Stedman's Medical Dictionary (28th ed ), p. 2072 (2006).
Kandadai et al., "Correct Performance of Pelvic Muscle Exercises in Women Reporting Prior Knowledge," Female Pelvic Med Reconstr Surg. 21 (3):135-40 (2015).
Moen et al., "Pelvic floor muscle function in women presenting with pelvic floor disorders," Int Urogynecol J Pelvic Floor Dysfunct. 20(7):843-6 (2009).
Rosenbaum, "Pelvic floor involvement in male and female sexual dysfunction and the role of pelvic floor rehabilitation in treatment: a literature review," J Sex Med. 4(1):4-13 (2007) (Abstract only) (2 pages).
Rosenblatt et al., "Interactive Pelvic Floor Muscle Training for Female Urinary Incontinence," Renovia, Inc., retrieved Apr. 30, 2019 from <https://renoviainc.com/wp-content/uploads/2018/04/REN005.01-White-Paper-12Apr18-FINAL.pdf> (2018) (6 pages).
Rosenbaum et al., "The Role of Pelvic Floor Pysical Therapy in the Treatment of Pelvic and Genital Pain-Related Sexual Dysfunction," J Sex Med. 5(3): 513-23 (2008).
International Search Report and Written Opinion for International Application No. PCT/US2019/027168, dated Aug. 12, 2019 (39 pages).
International Search Report and Written Opinion for International Application No. PCT/US2019/029400, dated Jul. 10, 2019 (17 pages).
Nygaard et al., "Efficacy of pelvic floor muscle exercises in women with stress, urge, and mixed urinary incontinence," Am J Obstet Gynecol. 174(1 Pt 1 ):120-125 (1996) (Abstract only).
Rosenblatt et al., "Evaluation of an accelerometer-based digital health system for the treatment of female urinary incontinence: A pilot study," Neurourol Urodyn. 38(7): 1944-1952 (2019).
International Search Report and Written Opinion for International Application No. PCT/US2019/058527, dated Feb. 21, 2020 (18 pages).
Office Action for Japanese Patent Application No. 2019-504938, dated May 18, 2021 (10 pages).
International Search Report and Written Opinion for International Application No. PCT/US2021/033155, dated Aug. 25, 2021 (19 pages).
Communication pursuant to Article 94(3) EPC for European Patent Application No. 15733078.8, dated Aug. 24, 2021 (8 pages).
Office Action for Japanese Patent Application No. 2020-143711, dated Sep. 8, 2021 (4 pages).

* cited by examiner

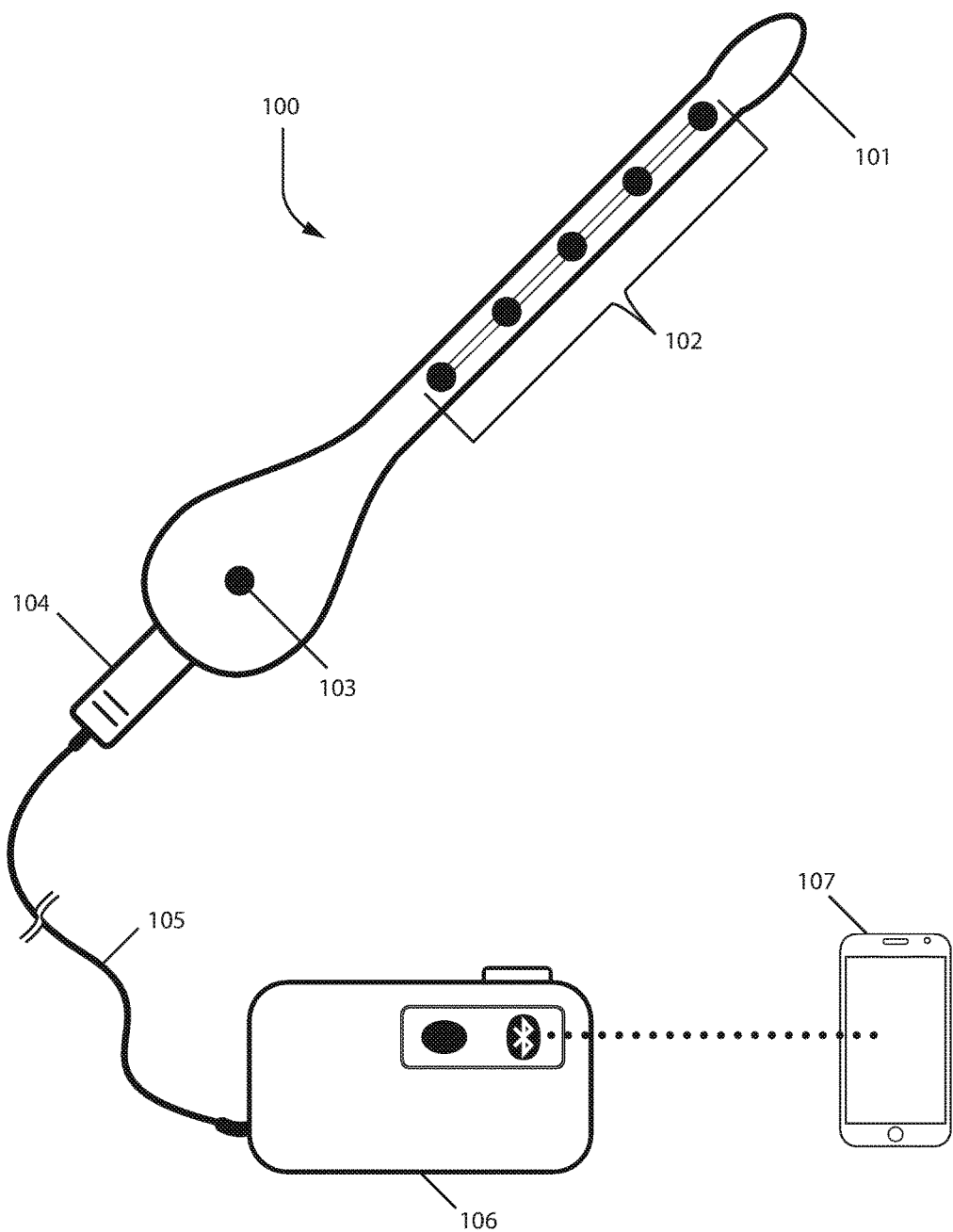

TREATMENT OF FECAL INCONTINENCE

CROSS-REFERENCE TO RELATED APPLICATIONS

This application is a continuation of U.S. patent application Ser. No. 14/581,547, filed Dec. 23, 2014, which is a continuation-in-part application of U.S. patent application Ser. No. 14/359,890, entitled "Treatment of Urinary Incontinence," filed May 21, 2014, which claims priority to international patent application PCT/US2012/066613, filed Nov. 27, 2012, and U.S. provisional Patent Application No. 61/563,889, filed Nov. 28, 2011, the entireties of which are incorporated herein by reference for all purposes.

BACKGROUND

The present embodiments relate to the devices, diagnosis, and treatment of fecal incontinence in females and males. The diagnosis and treatment may involve the use of a multiple sensor-enabled catheter capable of providing real-time data regarding the patient's anatomy and physiology, such as muscular function of the pelvic floor and rectal sphincter, as well as the position and movement of the catheter within the patient.

Fecal incontinence refers to the involuntary loss of gas or liquid stool (called minor incontinence) or the involuntary loss of solid stool (called major incontinence). An estimated 6.5 million Americans suffer with fecal incontinence, but the number of patients suffering from this condition is likely under-reported due to the embarrassment associated with the malady. The percentage of affected females is higher than males because of trauma to the pelvic floor musculature experienced during parturition. More specifically, female fecal incontinence can be caused by sphincter damage at the time of childbirth, injury to the muscles of the pelvic floor, or the innervation of these tissues. These injuries increase in direct proportion to the number of deliveries, the weight of the baby, and the number of operative deliveries. Cesarean section decreases the incidence of fecal incontinence in females, but carries the risks and complications of surgery. Other reasons for fecal incontinence in both females and males include constipation, chronic diarrhea, old age, depression, urinary incontinence, systemic diseases such as Irritable Bowel Syndrome (IBS), and problems involving the nervous system such as stroke, spinal cord injury, multiple sclerosis, and Parkinson's disease.

Current medical diagnostic tests for fecal incontinence include direct examination, anorectal manometry, sensory testing, anal endosonography, defecography, ultrasound, magnetic resonance imaging (MRI), pudenal nerve terminal latency (PNTML), and stool tests. Current treatments for fecal incontinence may involve changes in diet, pelvic floor muscle training (PFMT), medical therapy, and surgical correction.

PFMT (or Kegel) exercises includes a series of exercises designed to rehabilitate the musculature of the pelvic floor. For example, PFMT can help strengthen and tone the muscles under the uterus, bladder, and bowel (large intestine), and thus aid those who have problems with bowel control or rectal sphincter function. A current problem with PFMT, however, is that the individual is often unable to visualize or attain the proper muscle position and control to carry out an efficient and effective exercise regimen required to rehabilitate the pelvic floor muscles.

SUMMARY

The embodiments described herein relate to the diagnosis and treatment of fecal incontinence in females and males. In one embodiment, diagnosis and treatment involves the use of a probe device capable of providing real-time data regarding a patient's anatomy and physiology; such as muscular function of the rectal sphincter or pelvic floor, as well as the position or movement of the device within the patient. In one embodiment, the device may be a pressure sensor-enabled catheter.

In one embodiment, the multiple sensor-enabled catheter may include at least one sensor capable of providing real-time data of one or more types selected from the group consisting of position, movement, pressure, and flow. In this regard, a sensor may have a single measurement and reporting capability, or may have multiple measurement and reporting capabilities.

The present embodiments also provide for methods for the diagnosis or treatment of fecal incontinence in females and males, comprising positioning a multiple sensor-enabled catheter in a patient's rectum and determining the anatomical state of the patient, which treatment is capable of relieving or ameliorating incontinence. The anatomical state may be the sphincteric or supportive functions of the pelvic floor, such as muscle tone and strength. The method of diagnosis or treatment may also include manipulating the patient to relieve the fecal incontinence. The manipulation may be performed by the health care provider or the patient. The manipulation may include achieving a particular anatomical position of the patient's internal organs to achieve a particular muscular function of the pelvic floor.

The present embodiments contemplate the real-time position and movement tracking as described in U.S. Pat. No. 8,805,472. In this regard, the real-time position and movement tracking may include sensing the position of a fixed reference point(s) within the subject's body, by providing a catheter enabled with a sensor and capable of providing positional or movement data that can be perceived by a device, person, health care provider, or patient. The fixed reference point within the patient's body may be the pubic bone, the coccyx, the bladder, the urethra, the uterus, the prostate, or the rectum. The method may be performed in real-time, for example, during an operation. In another embodiment, the method may be performed at multiple time intervals. The multiple time intervals may occur, for example, pre- and post-event, wherein the event may be parturition, injury, or surgery.

BRIEF DESCRIPTION OF THE DRAWINGS

FIG. 1 depicts a view of an example probe device comprising a multiple sensor-enabled catheter.

DETAILED DESCRIPTION

All patents, applications, and other publications identified are expressly incorporated herein by reference for the purpose of describing and disclosing, for example, the devices methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and does not constitute any admission as to the correctness of the dates or contents of these documents.

As used herein and in the claims, the singular forms include the plural reference and vice versa unless clearly indicated otherwise by context. Throughout this specification and claims, unless otherwise indicated, "comprise," "comprises" and "comprising" are used inclusively rather than exclusively. The term "or" is inclusive unless modified, for example, by "either." Other than in the operating examples, or where otherwise indicated, all numbers should be understood as modified in all instances by the term "about."

Unless otherwise defined, scientific and technical terms used herein shall have the meanings that are commonly understood by those of skill in the art. The terminology used herein is for the purpose of describing particular embodiments only, and is not intended to limit the scope of the present invention, which is defined solely by the claims.

One embodiment described herein provides for methods for the diagnosis or treatment of fecal incontinence in females and males, comprising positioning in the rectum of a patient a multiple sensor-enabled catheter, visualizing the anatomical state of the patient, and manipulating the patient's body to a position capable of relieving the fecal incontinence. In an additional embodiment, the anatomical state is the relative position of one or more internal anatomical reference points selected from the pubic bone, the coccyx, the bladder, the urethra, the uterus, the prostate, or the rectum. In another embodiment, the anatomical state is the muscular function of the rectal sphincter.

An additional embodiment provides for a method of rehabilitating the pelvic floor musculature, comprising positioning in the rectum of a patient a multiple sensor-enabled catheter and visualizing the anatomical state of the patient, wherein the patient manipulates the catheter as a method of exercising control of sphincter or pelvic floor muscles.

In the present embodiments, for example, a catheter is enabled with at least one sensor capable of providing real-time data of at least one data type selected from the group consisting of position, movement, pressure, and flow. In this regard, a sensor may have a single measurement and reporting capability, or may have multiple measurement and reporting capabilities. The data obtained by the multiple sensor-enabled catheter may be reported in any number of ways know in the art, including the transmission to, and visualization on, a graphical user interface. For purposes of the embodiments, "real-time" may include instantaneous as well as delayed observation, reporting, or recording of an event as it elapses.

Advantageously, by viewing a real-time image of where one or more fixed anatomical reference points are located relative to one another during a procedure, a health care provider may manipulate the patient such that the patient is in a position capable of relieving or ameliorating fecal incontinence. In other instances, a patient may visualize her or his own anatomical state using the multiple sensor-enabled catheter, and may manipulate her or his body such that she or he is in a position capable of relieving fecal incontinence. Additionally or alternatively, the patient may visualize her or his own anatomical state using the multiple sensor-enabled catheter, and may manipulate her or his body to a position capable of controlling her or his pelvic floor muscles to relieve fecal incontinence.

A multiple sensor-enabled catheter provides a valuable study or diagnostic tool for a health care provider as well as a patient, particularly when the patient is considering surgery that may result in fecal incontinence as a post-surgical complication (e.g., from colorectal or prostate surgery). For example, a health care provider may provide the patient with an in-office procedure that determines a baseline position or relative mobilization of the an anatomical reference point within the patient's body (baseline) before possible damage to her or his pelvic floor; such that if surgical repair is subsequently performed, the bladder can be repositioned to the original, pre-incontinence anatomic position. Surgery could also be performed on patients with a surgically correctable structural defect, using the multiple sensor-enabled catheter to provide positioning data. Such procedures may involve a pelvic sling or other surgical intervention.

A multiple sensor-enabled catheter also provides a valuable study or diagnostic tool for a health care provider as well as a female patient pre- or post-childbirth. For example, a health care provider may provide a patient with an in-office procedure that determines a baseline position or relative mobilization of the an anatomical reference point within the patient's body (baseline) before possible damage to her pelvic floor, particularly injuries that result in pelvic organ prolapse; such that if surgical repair is subsequently performed, the bladder or prolapsed organs can be repositioned to the original, pre-incontinence anatomic position. With a female patient, another embodiment may involve a multiple sensor-enabled catheter inserted in the rectum and another multiple sensor-enabled catheter inserted in the vagina or urethra to provide additional positional or pressure data.

A multiple sensor-enabled catheter may incorporate at least one sensor capable of measuring or reporting data of various types, including position, movement, pressure, or flow. A multiple sensor-enabled catheter with more than one individual sensor may be arrayed as depicted in FIG. 1, or it may incorporate a single sensor that has multiple measurement and reporting capabilities.

The position or movement data may be of the sort measured or reported by any number of sensor devices, including accelerometer, gyroscope, inductive non-contact position sensor, string potentiometer, linear variable differential transformer, potentiometer, capacitive transducer, Eddy-current sensor, Hall effect sensor, optical proximity sensor, piezo-electric transducer, or photodiode array sensor devices. The position or movement data may also include magnetic, electromagnetic, microelectromechanical, radio frequency, ultrasound, or video data.

The pressure or flow data may be of the sort measured or reported by any number of sensor devices, including force collector types, such as piezo-resistive, capacitive, electromagnetic, piezo-electric, optical, potentiometric, or other types, such as resonant, thermal, ionization, ultrasonic, or density (mass and index of refraction) sensor devices.

For example, an embodiment of a multiple sensor enabled catheter comprising a firm tip, which may be about ½ inch in length to guide the catheter through the rectum. The catheter may be a Foley catheter. The number and precise placement of an individual sensor may vary depending on the type of positional, movement, pressure or flow measurement or reporting system employed. An individual sensor may have a single function or be multifunction (such as positional tracking combined with pressure and flow sensing). The multiple sensor-enabled catheter may also embody a video observation or recording device as well as an illumination source to facilitate such video capture. The precise placement of the sensor(s) and video capture component(s) are not pre-defined, and may be configured according to the requirements of the desired application.

EXAMPLES

As described herein, catheters useful in the present embodiments may embody at least one sensor capable of measuring and reporting at least one data type, including position, movement, pressure, and flow. These include, but are not limited to, magnetic, electromagnetic, microelectromechanical, radio frequency, ultrasound, and video. One example of a multiple sensor-enabled catheter, as shown in FIG. 1, is a probe or catheter 100 containing multiple sensors arranged in an array 102. The probe or catheter 100 may be constructed of a silicon or other material suitable for medical use in or on a patient's body. The probe or catheter 100 may include a distal probe or catheter tip 101, which may be constructed of a material with sufficient hardness or rigidity to facilitate the ease of insertion of the probe or catheter 100 into a patient's rectum. The probe or catheter 100 may also contain a proximal portion with a connector/handle 104 to facilitate positioning or movement of the probe or catheter 100 by the patient or health care provider. A sensor, such as a pressure sensor 103, may be contained in the proximal portion of the probe or catheter 100 to facilitate the assessment of rectal sphincter strength and/or control when the probe or catheter 100 is inserted into the patient's rectum.

In other embodiments, the sensor(s) may be positioned in the probe or catheter 100 without a particular spatial relationship to any other sensor(s). The probe or catheter 100 may contain a microelectromechanical (MEMS) device(s), a 3-axis accelerometer, a roll/pitch gyroscope and a yaw rate gyroscope, and a pressure and flow transducer. The devices may also be mounted on a small flexible printed circuit board (PCB) and then attached to the probe or catheter. The 3-axis accelerometer may track translation of the probe or catheter in three directions. The gyroscopes are utilized to account for gravitational rotation, allowing real-time movement to be tracked.

In one embodiment, a PCB may be prepared with the three MEMS devices mounted thereon. Soft leads trail the MEMS devices to supporting devices, including, for example, a data acquisition card which may be used for transforming analog signals to digital signals. The PCB is set within the wall of the probe or catheter. The location of the probe or catheter may be determined by the output signals of the MEMS devices.

The multiple sensor enabled catheter may be linked via data cable 105 to a transmitter 106, which can provide a wireless data signal (such as Bluetooth) to a device 107 (computer, tablet, smartphone, or similar device) capable of receiving the transmission of data collected by the sensors. The connection of the data cable 105 to the catheter or probe 100 may be achieved through a mating interface with connector/handle 104. Alternatively, the transmitter may be contained within the probe/catheter or the probe/catheter handle. The linked device 107 may process the data or provide a graphical user display, or transmit such information to another device(s) to accomplish similar tasks. In another embodiment, the probe or catheter 100 may transmit a wireless data signal directly to the device 107.

The patient may be asked to recreate maneuvers that induce fecal incontinence at the same time that the parameters for the location/pressure/flow/visualization of the anatomical reference point(s) are determined.

The patient's body (and the anatomical reference point(s)) may be manipulated to the position where rectal sphincter pressure is optimized and fecal continence is improved or restored to normal. These anatomical reference point positions may be displayed in real-time on a graphical user interface or recorded. The patient's body may be manipulated by a health care provider, or by the patient as described herein.

In the case of surgical intervention, if no pre-incontinence position is known, the patient's body (and the anatomical reference point(s)) may be positioned based on data collected from a cohort of patients with a similar fecal incontinence history or profile. Where pre-incontinence data is available (e.g., the positions of particular anatomical reference points are based on patient information from an earlier date), then at the time of surgery the corresponding anatomical reference points are repositioned to the location where the patient was previously fecally continent.

Following examination using the multiple sensor-enabled catheter, a health care provider may conclude that rehabilitation is an efficacious option for treating a patient's fecal incontinence. In this regard, the measurements provided by the multiple sensor-enabled catheter may be recorded to facilitate appropriate patient instructions on performing Kegel exercises in an optimal manner using the visual (on-screen) information provided by the catheter in real-time. Once engaging the proper musculature has been communicated successfully to a patient during a medical office visit, the patient may be sent home with the instructions to perform Kegel exercises five to six times daily, for example. Four to six weeks later, the patient may return for another examination using the multiple sensor-enabled catheter to evaluate rehabilitative treatment effectiveness, which may allow a health care provider to advise the patient about the prospects for restoring complete fecal continence with a continued rehabilitation regime or a surgical procedure.

Detailed embodiments are disclosed herein; however, it is to be understood that the disclosed embodiments are merely exemplary of the claimed invention that may be embodied in various forms. It will be appreciated that many modifications and other variations that will be appreciated by those skilled in the art are within the intended scope of this invention as claimed below without departing from the teachings, spirit, and intended scope of the invention.

What is claimed is:

1. A method for diagnosing or treating fecal incontinence in a patient comprising:
    a) inserting into the patient's rectum a device comprising a plurality of microelectromechanical (MEM) accelerometers and a plurality of pressure sensors positioned along a length of the device that extends into the rectum,
    b) obtaining position information from the MEM sensors of the device and displaying the position information on a graphical user interface to produce a first visual representation of a position of the patient's anatomy selected from one or more of a pubic bone, coccyx, bladder, urethra, uterus, prostate and rectum relative to at least one different anatomical reference point of the patient selected from the pubic bone, coccyx, bladder, urethra, uterus, prostate and rectum;
    c) obtaining pressure information from the pressure sensors of the device related to pressure imparted by the patient's rectal sphincter and displaying the pressure information on the graphical user interface; and
    d) using the position and pressure information to manipulate the anatomical state of the patient relative to the at least one different anatomical reference point to an anatomical position that relieves the incontinence, thereby diagnosing or treating the fecal incontinence.

2. The method of claim 1, wherein the method further comprises determining rectal sphincter muscular function.

3. The method of claim 1, wherein the method further comprises determining pelvic floor.

4. The method of claim 1, wherein the manipulating is performed by the patient.

5. The method of claim 1, wherein the manipulating is performed by a health care provider.

6. The method of claim 1, wherein the anatomical state of the patient is transmitted in real-time as wireless data to the graphical user interface.

7. The method of claim 1, wherein the manipulating comprises performing a pelvic floor muscle exercise.

8. The method of claim 7, wherein the pelvic floor muscle exercise is repeated one or more times.

9. The method of claim 1, wherein the manipulating comprises performing an exercise that strengthens a sphincter of the patient.

10. The method of claim 1, wherein the device comprises a handle and/or a connector for a wired connection to a transmitter.

11. The method of claim 1, wherein the method is performed during surgery.

* * * * *